(12) United States Patent
Zhou (10) Patent No.: US 8,105,269 B2
(45) Date of Patent: Jan. 31, 2012

(54) IN SITU TUBING MEASUREMENTS FOR INFUSION PUMPS

(75) Inventor: Yu Zhou, Vernon Hills, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 748 days.

(21) Appl. No.: 12/258,183

(22) Filed: Oct. 24, 2008

(65) Prior Publication Data

US 2010/0106082 A1   Apr. 29, 2010

(51) Int. Cl.
A61M 31/00 (2006.01)
G01C 25/00 (2006.01)
(52) U.S. Cl. .......................................... 604/67; 702/97
(58) Field of Classification Search ................... 702/97; 604/67
See application file for complete search history.

(56) References Cited

U.S. PATENT DOCUMENTS

| | | | |
|---|---|---|---|
| 3,606,596 A | 9/1971 | Edwards | |
| 3,756,752 A | 9/1973 | Stenner | |
| 3,771,694 A | 11/1973 | Kaminski | |
| 3,809,871 A | 5/1974 | Howard et al. | |
| 3,850,026 A * | 11/1974 | Lund et al. | 73/622 |
| 3,998,103 A | 12/1976 | Bjorklund et al. | |
| 4,038,983 A | 8/1977 | Mittleman et al. | |
| D246,258 S | 11/1977 | Ekert | |
| 4,065,230 A | 12/1977 | Gezari | |
| 4,078,562 A | 3/1978 | Friedman | |
| 4,151,407 A | 4/1979 | McBride et al. | |
| RE30,088 E * | 9/1979 | Lund et al. | 73/622 |
| 4,187,057 A | 2/1980 | Xanthopoulos | |
| 4,199,307 A | 4/1980 | Jassawalla | |
| 4,237,409 A | 12/1980 | Sugalski | |
| 4,256,437 A | 3/1981 | Brown | |
| 4,273,121 A | 6/1981 | Jassawalla | |
| 4,276,004 A | 6/1981 | Hahn | |
| 4,277,226 A | 7/1981 | Archibald | |

(Continued)

FOREIGN PATENT DOCUMENTS

EP          0215249         3/1987
(Continued)

OTHER PUBLICATIONS

International Search Report for International Application No. PCT/US 02/36963 of Applicant Baxter International Inc.

(Continued)

*Primary Examiner* — Lisa Caputo
*Assistant Examiner* — Jonathan Dunlap
(74) *Attorney, Agent, or Firm* — K&L Gates LLP (57) ABSTRACT

An infusion pump uses sensors and a computer program to detect tubing in a tube-loading section of the pump. The pump and the computer program also measures one or more of the tubing outer diameter, outer circumference, inner diameter, inner circumference, and tubing wall thickness. The infusion pump utilizes proximity sensors, such as an ultrasonic sensor, a capacitive sensor, or even an air-in-line sensor to detect proximity between two infusion pump surfaces, such as the surfaces that clamp the tubing in the pump, to determine thickness. At least one of the clamping surfaces is equipped with sensors to indicate contact length of the tubing with the surface. Using these measurements, the tubing wall thickness and inner diameter can be determined. Knowing the actual tubing inner diameter, increased volumetric accuracy is possible, up to a three or four percent improvement over present measurements.

20 Claims, 8 Drawing Sheets

U.S. PATENT DOCUMENTS

| | | |
|---|---|---|
| 4,308,866 A | 1/1982 | Jelliffe et al. |
| 4,320,757 A | 3/1982 | Whitney et al. |
| D263,997 S | 4/1982 | Preussner |
| 4,332,246 A | 6/1982 | Thomson |
| 4,369,780 A | 1/1983 | Sakai |
| 4,373,525 A | 2/1983 | Kobayashi |
| D268,206 S | 3/1983 | Kosako |
| 4,392,849 A | 7/1983 | Petre et al. |
| 4,398,908 A | 8/1983 | Siposs |
| 4,416,595 A | 11/1983 | Cromie |
| 4,428,381 A | 1/1984 | Hepp |
| 4,430,078 A | 2/1984 | Sprague |
| 4,443,216 A | 4/1984 | Chappell |
| 4,445,535 A | 5/1984 | Mayfield |
| 4,447,233 A | 5/1984 | Mayfield |
| 4,447,234 A | 5/1984 | Mayfield |
| 4,451,255 A | 5/1984 | Bujan et al. |
| 4,457,751 A | 7/1984 | Rodler |
| 4,460,358 A | 7/1984 | Somerville et al. |
| 4,468,221 A | 8/1984 | Mayfield |
| 4,472,116 A | 9/1984 | Wenstrup |
| 4,487,604 A | 12/1984 | Iwatschenko et al. |
| 4,493,710 A | 1/1985 | King et al. |
| 4,496,351 A | 1/1985 | Hillel et al. |
| 4,498,843 A | 2/1985 | Schneider et al. |
| D278,181 S | 3/1985 | Archibald et al. |
| 4,504,200 A | 3/1985 | Olson |
| 4,511,352 A | 4/1985 | Theeuwes et al. |
| D278,743 S | 5/1985 | Manno et al. |
| 4,519,792 A | 5/1985 | Dawe |
| 4,529,401 A | 7/1985 | Leslie et al. |
| 4,537,561 A | 8/1985 | Xanthopoulos |
| 4,544,369 A | 10/1985 | Skakoon et al. |
| 4,551,133 A | 11/1985 | Zegers de Beyl et al. |
| 4,559,038 A | 12/1985 | Berg et al. |
| 4,561,830 A | 12/1985 | Bradley |
| 4,561,856 A | 12/1985 | Cochran |
| 4,562,751 A | 1/1986 | Nason et al. |
| 4,565,542 A | 1/1986 | Berg |
| 4,585,009 A | 4/1986 | Barker et al. |
| 4,585,941 A | 4/1986 | Bergner |
| 4,596,550 A | 6/1986 | Troutner |
| 4,601,702 A | 7/1986 | Hudson |
| 4,602,249 A | 7/1986 | Abbott |
| 4,624,661 A | 11/1986 | Arimond |
| D287,053 S | 12/1986 | Bucchianeri et al. |
| D287,277 S | 12/1986 | Kosako et al. |
| 4,637,817 A | 1/1987 | Archibald et al. |
| 4,639,245 A | 1/1987 | Pastrone et al. |
| 4,646,781 A | 3/1987 | McIntyre et al. |
| 4,648,812 A | 3/1987 | Kobayashi et al. |
| 4,650,469 A | 3/1987 | Berg et al. |
| 4,652,262 A | 3/1987 | Veracchi |
| 4,653,987 A | 3/1987 | Tsuji et al. |
| 4,657,490 A | 4/1987 | Abbott |
| 4,666,430 A | 5/1987 | Brown et al. |
| 4,668,220 A | 5/1987 | Hawrylenko |
| 4,676,776 A | 6/1987 | Howson |
| 4,678,408 A | 7/1987 | Nason et al. |
| 4,681,563 A | 7/1987 | Deckert et al. |
| 4,685,903 A | 8/1987 | Cable et al. |
| 4,690,673 A | 9/1987 | Bloomquist |
| 4,696,671 A | 9/1987 | Epstein et al. |
| D293,468 S | 12/1987 | Hill et al. |
| 4,714,462 A | 12/1987 | DiDomenico |
| 4,718,576 A | 1/1988 | Tamura et al. |
| 4,718,893 A | 1/1988 | Dorman et al. |
| 4,722,149 A | 2/1988 | Weaver et al. |
| 4,722,224 A | 2/1988 | Scheller et al. |
| 4,722,734 A | 2/1988 | Kolln |
| 4,725,205 A | 2/1988 | Cannon et al. |
| 4,731,058 A | 3/1988 | Doan |
| D295,320 S | 4/1988 | Vaughan |
| 4,741,732 A | 5/1988 | Crankshaw et al. |
| 4,741,736 A | 5/1988 | Brown |
| 4,744,786 A | 5/1988 | Hooven |
| 4,754,401 A | 6/1988 | Kaczynski et al. |
| 4,756,706 A | 7/1988 | Kerns et al. |
| 4,758,228 A | 7/1988 | Williams |
| 4,759,527 A | 7/1988 | Brown |
| 4,772,263 A | 9/1988 | Dorman et al. |
| 4,781,548 A | 11/1988 | Alderson et al. |
| 4,804,368 A | 2/1989 | Skakoon et al. |
| 4,810,243 A | 3/1989 | Howson |
| 4,834,704 A | 5/1989 | Reinicke |
| 4,836,752 A | 6/1989 | Burkett |
| 4,838,857 A | 6/1989 | Strowe et al. |
| 4,838,860 A | 6/1989 | Groshong et al. |
| 4,840,542 A | 6/1989 | Abbott |
| 4,846,637 A | 7/1989 | Alderson et al. |
| 4,854,324 A | 8/1989 | Hirschman et al. |
| 4,856,339 A | 8/1989 | Williams |
| 4,882,575 A | 11/1989 | Kawahara |
| D305,060 S | 12/1989 | Bisha' et al. |
| 4,886,431 A | 12/1989 | Soderquist et al. |
| 4,890,984 A | 1/1990 | Alderson et al. |
| 4,898,579 A | 2/1990 | Groshong et al. |
| 4,900,305 A | 2/1990 | Smith et al. |
| 4,908,017 A | 3/1990 | Howson et al. |
| 4,911,168 A | 3/1990 | Davis |
| 4,919,650 A | 4/1990 | Feingold et al. |
| 4,923,375 A | 5/1990 | Ejlersen |
| 4,931,041 A | 6/1990 | Faeser |
| 4,936,760 A | 6/1990 | Williams |
| D309,662 S | 7/1990 | Gorton |
| 4,941,808 A | 7/1990 | Qureshi et al. |
| 4,943,279 A | 7/1990 | Samiotes et al. |
| 4,954,046 A | 9/1990 | Irvin et al. |
| 4,960,230 A | 10/1990 | Marelli |
| 4,976,151 A | 12/1990 | Morishita |
| 4,978,335 A | 12/1990 | Arthur, III |
| 5,000,739 A | 3/1991 | Kulisz et al. |
| 5,006,050 A | 4/1991 | Cooke et al. |
| 5,011,378 A | 4/1991 | Brown et al. |
| 5,017,192 A | 5/1991 | Dodge et al. |
| 5,018,945 A | 5/1991 | D'Silva |
| 5,034,004 A | 7/1991 | Crankshaw |
| 5,041,086 A | 8/1991 | Koenig et al. |
| 5,044,900 A | 9/1991 | Cavallaro |
| 5,049,047 A * | 9/1991 | Polaschegg et al. .......... 417/474 |
| 5,053,031 A | 10/1991 | Borsanyi |
| 5,055,001 A | 10/1991 | Natwick et al. |
| 5,057,081 A | 10/1991 | Sunderland |
| 5,061,243 A | 10/1991 | Winchell et al. |
| D321,559 S | 11/1991 | Kienholz |
| 5,078,362 A | 1/1992 | Lawless et al. |
| 5,078,683 A | 1/1992 | Sancoff et al. |
| 5,080,653 A | 1/1992 | Voss et al. |
| 5,088,904 A | 2/1992 | Okada |
| 5,098,256 A | 3/1992 | Smith |
| 5,098,377 A | 3/1992 | Borsanyi et al. |
| 5,100,380 A | 3/1992 | Epstein et al. |
| 5,100,389 A | 3/1992 | Vaillancourt |
| 5,102,392 A | 4/1992 | Sakai et al. |
| 5,104,374 A | 4/1992 | Bishko et al. |
| D326,153 S | 5/1992 | Eastman et al. |
| 5,116,203 A | 5/1992 | Natwick et al. |
| 5,120,096 A | 6/1992 | D'Silva |
| 5,123,275 A | 6/1992 | Daoud et al. |
| 5,131,816 A | 7/1992 | Brown et al. |
| D328,952 S | 8/1992 | Arioka |
| 5,135,500 A | 8/1992 | Zdeb |
| 5,153,827 A | 10/1992 | Coutre et al. |
| 5,160,320 A | 11/1992 | Yum et al. |
| 5,165,874 A | 11/1992 | Sancoff et al. |
| 5,167,633 A | 12/1992 | Mann et al. |
| 5,176,004 A | 1/1993 | Gaudet |
| 5,176,644 A | 1/1993 | Srisathapat et al. |
| 5,177,993 A | 1/1993 | Beckman et al. |
| 5,181,842 A | 1/1993 | Sunderland et al. |
| 5,181,910 A | 1/1993 | Scanlon |
| 5,197,322 A | 3/1993 | Indravudh |
| 5,199,852 A | 4/1993 | Danby |
| 5,207,645 A | 5/1993 | Ross et al. |
| 5,213,483 A | 5/1993 | Flaherty et al. |
| 5,217,442 A | 6/1993 | Davis |
| 5,219,327 A | 6/1993 | Okada |

| | | | | | |
|---|---|---|---|---|---|
| 5,219,330 A | 6/1993 | Bollish et al. | 5,485,408 A | 1/1996 | Blomquist |
| 5,219,331 A | 6/1993 | Vanderveen | D367,527 S | 2/1996 | Marston et al. |
| 5,219,428 A | 6/1993 | Stern | D367,528 S | 2/1996 | Marston et al. |
| 5,232,449 A | 8/1993 | Stern et al. | 5,489,265 A | 2/1996 | Montalvo et al. |
| 5,236,416 A | 8/1993 | McDaniel et al. | 5,501,665 A | 3/1996 | Jhuboo et al. |
| 5,238,001 A | 8/1993 | Gallant et al. | 5,503,538 A | 4/1996 | Wiernicki et al. |
| D339,193 S | 9/1993 | Thompson et al. | 5,505,709 A | 4/1996 | Funderburk et al. |
| 5,242,407 A | 9/1993 | Struble et al. | 5,507,412 A | 4/1996 | Ebert et al. |
| 5,242,408 A | 9/1993 | Jhuboo et al. | 5,511,951 A | 4/1996 | O'Leary |
| 5,244,461 A | 9/1993 | Derlien | 5,513,957 A | 5/1996 | O'Leary |
| 5,244,463 A | 9/1993 | Cordner, Jr. et al. | 5,514,103 A | 5/1996 | Srisathapat et al. |
| 5,254,096 A | 10/1993 | Rondelet et al. | 5,520,638 A | 5/1996 | O'Quinn et al. |
| 5,256,157 A | 10/1993 | Samioles et al. | D371,194 S | 6/1996 | Marston et al. |
| 5,257,971 A | 11/1993 | Lord et al. | 5,522,798 A | 6/1996 | Johnson et al. |
| 5,261,884 A | 11/1993 | Stern et al. | 5,522,799 A | 6/1996 | Furukawa |
| 5,265,431 A | 11/1993 | Gaudet et al. | 5,527,307 A | 6/1996 | Srisathapat et al. |
| D342,231 S | 12/1993 | Walker et al. | 5,529,214 A | 6/1996 | Lasonde et al. |
| 5,276,610 A | 1/1994 | Maeda et al. | 5,531,680 A | 7/1996 | Dumas et al. |
| 5,279,556 A | 1/1994 | Goi et al. | 5,531,697 A | 7/1996 | Olsen et al. |
| 5,281,111 A | 1/1994 | Plambeck et al. | 5,533,981 A | 7/1996 | Mandro et al. |
| 5,290,239 A | 3/1994 | Classey et al. | 5,545,140 A | 8/1996 | Conero et al. |
| 5,295,966 A | 3/1994 | Stern et al. | 5,547,470 A | 8/1996 | Johnson et al. |
| 5,295,967 A | 3/1994 | Rondelet et al. | 5,549,460 A | 8/1996 | O'Leary |
| 5,298,021 A | 3/1994 | Sherer | 5,551,850 A | 9/1996 | Williamson et al. |
| D347,472 S | 5/1994 | Sunderland et al. | 5,554,115 A | 9/1996 | Thomas et al. |
| 5,308,333 A | 5/1994 | Skakoon | 5,554,123 A | 9/1996 | Herskowitz |
| 5,308,335 A | 5/1994 | Ross et al. | 5,562,621 A | 10/1996 | Claude et al. |
| 5,317,506 A | 5/1994 | Coutre et al. | 5,569,186 A | 10/1996 | Lord et al. |
| D348,101 S | 6/1994 | Poli et al. | 5,573,502 A | 11/1996 | LeCocq et al. |
| 5,321,392 A | 6/1994 | Skakoon et al. | 5,573,506 A | 11/1996 | Vasko |
| D348,730 S | 7/1994 | Walker et al. | 5,578,077 A | 11/1996 | Kassatly |
| 5,326,236 A | 7/1994 | Kramer et al. | D376,848 S | 12/1996 | Zelig et al. |
| 5,328,460 A | 7/1994 | Lord et al. | 5,584,811 A | 12/1996 | Ross et al. |
| 5,330,431 A | 7/1994 | Herskowitz | 5,586,629 A | 12/1996 | Shoberg et al. |
| 5,336,245 A | 8/1994 | Adams et al. | 5,588,815 A | 12/1996 | Zaleski, II |
| 5,338,157 A | 8/1994 | Blomquist | 5,601,420 A | 2/1997 | Warner et al. |
| 5,341,291 A | 8/1994 | Roizen et al. | 5,609,575 A | 3/1997 | Larson et al. |
| 5,343,734 A | 9/1994 | Maeda et al. | 5,620,312 A | 4/1997 | Hyman et al. |
| 5,348,539 A | 9/1994 | Herskowitz | RE35,501 E | 5/1997 | Ross et al. |
| 5,356,379 A | 10/1994 | Vaillancourt | 5,628,619 A | 5/1997 | Wilson |
| D352,778 S | 11/1994 | Irvin et al. | 5,630,710 A | 5/1997 | Tune et al. |
| 5,366,904 A | 11/1994 | Qureshi et al. | D380,260 S | 6/1997 | Hyman |
| D353,667 S | 12/1994 | Tsubota et al. | 5,637,093 A | 6/1997 | Hyman et al. |
| 5,370,612 A | 12/1994 | Maeda et al. | 5,637,095 A | 6/1997 | Nason et al. |
| 5,370,622 A | 12/1994 | Livingston et al. | 5,643,212 A | 7/1997 | Coutre et al. |
| 5,374,251 A | 12/1994 | Smith | 5,647,853 A | 7/1997 | Feldmann et al. |
| 5,374,965 A | 12/1994 | Kanno | 5,647,854 A | 7/1997 | Olsen et al. |
| 5,376,070 A | 12/1994 | Purvis et al. | 5,665,070 A | 9/1997 | McPhee |
| 5,378,231 A | 1/1995 | Johnson et al. | 5,669,877 A | 9/1997 | Blomquist |
| 5,382,236 A | 1/1995 | Otto et al. | 5,673,588 A | 10/1997 | Raymond |
| D355,716 S | 2/1995 | Nash et al. | 5,681,284 A | 10/1997 | Herskowitz |
| 5,387,088 A | 2/1995 | Knapp et al. | 5,681,285 A | 10/1997 | Ford et al. |
| 5,389,078 A | 2/1995 | Zalesky et al. | 5,683,367 A | 11/1997 | Jordan et al. |
| 5,395,320 A | 3/1995 | Padda et al. | 5,685,844 A | 11/1997 | Marttila |
| 5,395,324 A | 3/1995 | Hinrichs et al. | 5,695,464 A | 12/1997 | Viallet |
| 5,395,340 A | 3/1995 | Lee | 5,695,473 A | 12/1997 | Olsen |
| 5,397,222 A | 3/1995 | Moss et al. | D390,654 S | 2/1998 | Alsberg et al. |
| 5,411,482 A | 5/1995 | Campbell | 5,713,856 A | 2/1998 | Eggers et al. |
| 5,415,532 A | 5/1995 | Loughnane et al. | 5,722,957 A | 3/1998 | Steinbach |
| 5,419,684 A | 5/1995 | Struble et al. | 5,743,878 A | 4/1998 | Ross et al. |
| 5,423,746 A | 6/1995 | Burkett et al. | 5,745,378 A | 4/1998 | Barker et al. |
| 5,423,759 A | 6/1995 | Campbell | 5,752,976 A | 5/1998 | Duffin et al. |
| 5,429,602 A | 7/1995 | Hauser | 5,764,034 A | 6/1998 | Bowman et al. |
| 5,431,627 A | 7/1995 | Pastrone et al. | 5,766,155 A | 6/1998 | Hyman et al. |
| 5,433,704 A | 7/1995 | Ross et al. | 5,769,823 A | 6/1998 | Otto |
| 5,433,710 A | 7/1995 | VanAntwerp et al. | 5,776,345 A | 7/1998 | Truitt et al. |
| D361,379 S | 8/1995 | Sancoff et al. | 5,782,805 A | 7/1998 | Meinzer et al. |
| D361,617 S | 8/1995 | Sancoff et al. | 5,785,681 A | 7/1998 | Indravudh |
| 5,437,635 A | 8/1995 | Fields et al. | D397,432 S | 8/1998 | Rake et al. |
| 5,437,642 A | 8/1995 | Thill et al. | 5,788,669 A | 8/1998 | Peterson |
| 5,458,469 A | 10/1995 | Hauser | 5,791,880 A | 8/1998 | Wilson |
| 5,458,578 A | 10/1995 | Sebesta et al. | 5,795,327 A | 8/1998 | Wilson et al. |
| 5,462,051 A | 10/1995 | Oka et al. | 5,807,322 A | 9/1998 | Lindsey et al. |
| 5,462,525 A | 10/1995 | Srisathapat et al. | 5,807,336 A | 9/1998 | Russo et al. |
| 5,466,218 A | 11/1995 | Srisathapat et al. | 5,813,972 A | 9/1998 | Nazarian et al. |
| 5,472,317 A | 12/1995 | Field et al. | 5,814,015 A | 9/1998 | Gargano et al. |
| 5,472,420 A | 12/1995 | Campbell | 5,814,019 A | 9/1998 | Steinbach et al. |
| 5,478,211 A | 12/1995 | Dominiak et al. | 5,836,915 A | 11/1998 | Steinbach et al. |
| 5,482,446 A | 1/1996 | Williamson et al. | 5,840,058 A | 11/1998 | Ammann et al. |

| Patent | Kind | Date | Inventor |
|---|---|---|---|
| 5,842,841 | A | 12/1998 | Danby et al. |
| D404,813 | S | 1/1999 | Hauser |
| 5,868,710 | A | 2/1999 | Battiato et al. |
| 5,871,465 | A | 2/1999 | Vasko |
| 5,885,245 | A | 3/1999 | Lynch et al. |
| D408,911 | S | 4/1999 | Moubayed et al. |
| 5,894,273 | A | 4/1999 | Meador et al. |
| 5,895,371 | A | 4/1999 | Levitas et al. |
| 5,897,530 | A | 4/1999 | Jackson |
| 5,904,668 | A | 5/1999 | Hyman et al. |
| 5,908,414 | A | 6/1999 | Otto et al. |
| 5,935,099 | A | 8/1999 | Peterson et al. |
| 5,935,106 | A | 8/1999 | Olsen |
| 5,943,633 | A | 8/1999 | Wilson et al. |
| 5,951,510 | A | 9/1999 | Barak |
| 5,954,696 | A | 9/1999 | Ryan |
| 5,954,697 | A | 9/1999 | Srisathapat et al. |
| 5,957,890 | A | 9/1999 | Mann et al. |
| 5,988,983 | A * | 11/1999 | Furusawa ............... 417/43 |
| 5,993,420 | A | 11/1999 | Hyman et al. |
| 6,004,020 | A | 12/1999 | Bartur |
| 6,013,057 | A | 1/2000 | Danby et al. |
| D420,737 | S | 2/2000 | Kivlehan |
| 6,024,539 | A | 2/2000 | Blomquist |
| 6,078,273 | A | 6/2000 | Hutchins et al. |
| 6,083,201 | A | 7/2000 | Skinkle |
| D430,288 | S | 8/2000 | Mason et al. |
| D430,289 | S | 8/2000 | Mason et al. |
| 6,095,757 | A | 8/2000 | Frezza |
| 6,106,498 | A | 8/2000 | Friedli et al. |
| 6,110,152 | A | 8/2000 | Kovelman |
| 6,117,115 | A * | 9/2000 | Hill et al. ............... 604/250 |
| 6,123,524 | A | 9/2000 | Danby et al. |
| 6,129,517 | A | 10/2000 | Danby et al. |
| 6,135,949 | A | 10/2000 | Russo et al. |
| 6,139,748 | A | 10/2000 | Ericson et al. |
| D434,142 | S | 11/2000 | Cheney, II et al. |
| 6,145,695 | A | 11/2000 | Garrigues |
| 6,173,198 | B1 | 1/2001 | Schulze et al. |
| 6,195,887 | B1 | 3/2001 | Danby et al. |
| 6,203,528 | B1 | 3/2001 | Deckert et al. |
| 6,213,723 | B1 | 4/2001 | Danby et al. |
| 6,213,738 | B1 | 4/2001 | Danby et al. |
| 6,231,560 | B1 | 5/2001 | Bui et al. |
| 6,269,340 | B1 | 7/2001 | Ford et al. |
| D446,854 | S | 8/2001 | Cheney, II et al. |
| 6,270,478 | B1 | 8/2001 | Mernøe |
| 6,280,416 | B1 | 8/2001 | Van Antwerp et al. |
| D447,558 | S | 9/2001 | Cartledge et al. |
| 6,297,795 | B1 | 10/2001 | Kato et al. |
| 6,305,908 | B1 | 10/2001 | Hermann et al. |
| D453,830 | S | 2/2002 | McDowell et al. |
| 6,347,553 | B1 | 2/2002 | Morris et al. |
| 6,348,043 | B1 | 2/2002 | Hagen et al. |
| 6,348,952 | B1 | 2/2002 | Jeong |
| 6,358,225 | B1 | 3/2002 | Butterfield |
| D457,949 | S | 5/2002 | Krug et al. |
| 6,398,760 | B1 | 6/2002 | Danby |
| 6,413,239 | B1 | 7/2002 | Burns et al. |
| 6,423,035 | B1 | 7/2002 | Das et al. |
| D461,241 | S | 8/2002 | Moberg et al. |
| D461,891 | S | 8/2002 | Moberg |
| D462,121 | S | 8/2002 | Cartledge et al. |
| 6,458,102 | B1 | 10/2002 | Mann et al. |
| 6,471,436 | B1 | 10/2002 | Gjata et al. |
| 6,475,180 | B2 | 11/2002 | Peterson et al. |
| 6,485,465 | B2 | 11/2002 | Moberg et al. |
| 6,489,896 | B1 | 12/2002 | Platt et al. |
| 6,500,151 | B1 | 12/2002 | Cobb et al. |
| 6,519,569 | B1 | 2/2003 | White et al. |
| 6,544,229 | B1 | 4/2003 | Danby et al. |
| 6,554,822 | B1 | 4/2003 | Holschneider et al. |
| D474,837 | S | 5/2003 | Gillespie, Jr. et al. |
| D475,454 | S | 6/2003 | Gillespie, Jr. et al. |
| 6,572,604 | B1 | 6/2003 | Platt et al. |
| 6,585,675 | B1 | 7/2003 | O'Mahony et al. |
| 6,592,551 | B1 | 7/2003 | Cobb |
| D479,323 | S | 9/2003 | Gillespie, Jr. et al. |
| 6,620,151 | B2 | 9/2003 | Blischak et al. |
| 6,648,861 | B2 | 11/2003 | Platt et al. |
| 6,652,493 | B1 | 11/2003 | Das |
| 6,656,148 | B2 | 12/2003 | Das et al. |
| 6,659,980 | B2 | 12/2003 | Moberg et al. |
| 6,666,845 | B2 | 12/2003 | Hooper et al. |
| 6,692,241 | B2 | 2/2004 | Watanabe et al. |
| 6,755,814 | B2 | 6/2004 | Wieland et al. |
| 6,776,773 | B2 | 8/2004 | Kiyatake et al. |
| 6,800,069 | B2 | 10/2004 | Lampropoulos et al. |
| 6,805,687 | B2 | 10/2004 | Dextradeur et al. |
| 6,827,702 | B2 | 12/2004 | Lebel et al. |
| 6,854,620 | B2 | 2/2005 | Ramey |
| 6,945,954 | B2 | 9/2005 | Hochman et al. |
| 6,999,854 | B2 | 2/2006 | Roth |
| 7,008,403 | B1 | 3/2006 | Mallett |
| 7,018,361 | B2 | 3/2006 | Gillespie, Jr. et al. |
| 7,022,107 | B1 | 4/2006 | Christensen et al. |
| 7,025,226 | B2 | 4/2006 | Ramey |
| 7,029,455 | B2 | 4/2006 | Flaherty |
| 7,092,796 | B2 | 8/2006 | Vanderveen |
| 7,182,750 | B2 | 2/2007 | Lampropoulos et al. |
| 7,193,521 | B2 | 3/2007 | Moberg et al. |
| 7,232,423 | B2 | 6/2007 | Mernoe |
| 7,236,936 | B2 | 6/2007 | White et al. |
| 7,255,683 | B2 | 8/2007 | Vanderveen et al. |
| 7,306,578 | B2 | 12/2007 | Gray et al. |
| 7,322,961 | B2 | 1/2008 | Forrest |
| 7,338,464 | B2 | 3/2008 | Blischak et al. |
| 7,341,581 | B2 | 3/2008 | Mallett |
| 7,347,837 | B2 | 3/2008 | Azzolini |
| 7,351,226 | B1 | 4/2008 | Herskowitz |
| 7,356,382 | B2 | 4/2008 | Vanderveen |
| 7,374,556 | B2 | 5/2008 | Mallett |
| D574,016 | S | 7/2008 | Yodfat et al. |
| D577,118 | S | 9/2008 | Yodfat et al. |
| 7,471,994 | B2 | 12/2008 | Ford et al. |
| 7,534,226 | B2 | 5/2009 | Mernoe et al. |
| 7,559,926 | B1 | 7/2009 | Blischak |
| 7,569,030 | B2 | 8/2009 | Lebel et al. |
| 7,601,148 | B2 | 10/2009 | Keller |
| 7,608,060 | B2 | 10/2009 | Gillespie, Jr. et al. |
| 7,611,498 | B2 | 11/2009 | Hasler |
| 7,621,893 | B2 | 11/2009 | Moberg et al. |
| 7,632,249 | B2 | 12/2009 | Momeni et al. |
| 7,637,892 | B2 | 12/2009 | Steinbach et al. |
| 7,647,237 | B2 | 1/2010 | Malave et al. |
| D612,484 | S | 3/2010 | Yodfat et al. |
| D614,587 | S | 4/2010 | Yodfat et al. |
| 7,708,717 | B2 | 5/2010 | Estes et al. |
| 7,717,903 | B2 | 5/2010 | Estes et al. |
| 7,725,272 | B2 | 5/2010 | Ginggen et al. |
| 7,743,975 | B2 | 6/2010 | Miller |
| 7,758,552 | B2 | 7/2010 | Zoltan et al. |
| 7,766,863 | B2 | 8/2010 | Gillespie, Jr. et al. |
| 7,766,873 | B2 | 8/2010 | Moberg et al. |
| 7,776,029 | B2 | 8/2010 | Whitehurst et al. |
| 7,776,030 | B2 | 8/2010 | Estes et al. |
| 7,789,859 | B2 | 9/2010 | Estes et al. |
| 7,794,426 | B2 | 9/2010 | Briones et al. |
| 7,794,427 | B2 | 9/2010 | Estes et al. |
| 7,794,428 | B2 | 9/2010 | Estes et al. |
| 7,803,134 | B2 | 9/2010 | Sharifi et al. |
| 7,833,196 | B2 | 11/2010 | Estes et al. |
| 7,837,651 | B2 | 11/2010 | Bishop et al. |
| 7,850,641 | B2 | 12/2010 | Lebel et al. |
| 2001/0031944 | A1 | 10/2001 | Peterson et al. |
| 2001/0034502 | A1 | 10/2001 | Moberg et al. |
| 2002/0004645 | A1 | 1/2002 | Carlisle et al. |
| 2002/0128606 | A1 | 9/2002 | Cowan et al. |
| 2002/0165491 | A1 | 11/2002 | Reilly |
| 2003/0009133 | A1 | 1/2003 | Ramey |
| 2003/0060754 | A1 | 3/2003 | Reilly et al. |
| 2003/0060768 | A1 | 3/2003 | Kiyatake et al. |
| 2003/0065287 | A1 | 4/2003 | Spohn et al. |
| 2003/0073954 | A1 | 4/2003 | Moberg et al. |
| 2003/0078534 | A1 | 4/2003 | Hochman et al. |
| 2003/0097092 | A1 | 5/2003 | Flaherty |
| 2003/0149402 | A1 | 8/2003 | Gerlach et al. |

FOREIGN PATENT DOCUMENTS

| | | |
|---|---|---|
| EP | 0374618 | 6/1990 |
| EP | 0447985 | 9/1991 |
| EP | 0522527 | 1/1993 |
| EP | 0560270 | 9/1993 |
| EP | 0567944 | 11/1993 |
| EP | 0567945 | 11/1993 |
| EP | 0567946 | 11/1993 |
| EP | 0567962 | 11/1993 |
| EP | 0881388 | 12/1998 |
| EP | 1834658 | 9/2008 |
| EP | 2062605 | 5/2009 |
| GB | 2190145 | 11/1987 |
| GB | 2208897 | 4/1989 |
| GB | 2336510 | 10/1999 |
| WO | WO84/04685 | 12/1984 |
| WO | WO92/03656 | 3/1992 |
| WO | WO93/05829 | 4/1993 |
| WO | WO95/17913 | 7/1995 |
| WO | WO00/42911 | 7/2000 |
| WO | WO00/48112 | 8/2000 |
| WO | WO00/68766 | 11/2000 |

OTHER PUBLICATIONS

International Search Report for International Application No. PCT/US 02/36964 of Applicant Baxter International Inc.

Written Opinion for PCT/US2009/061169 dated Mar. 3, 2010.

\* cited by examiner

TUBING OD TEST

FIG. 8A

TUBING THICKNESS TEST

FIG. 12C $$\Delta l = -(\pi/2)\Delta d \quad (2)$$
$$l = l_1 + \Delta l$$
$$d = d_2$$
$$R_0 = d/2 + l/\pi \quad (1)$$

IN SITU TUBING MEASUREMENTS FOR INFUSION PUMPS

BACKGROUND

The field of the present disclosure invention is infusion pumps and relates generally to systems, apparatuses, and methods for pumping or infusing volumes of medical fluids to a patient, typically via an intravenous route.

Infusion pumps are used to infuse drugs and liquids into patients, typically via intravenous lines. While some infusion pumps deal with relatively large volumes, there may be more interest in pumps with a capability of delivering only very small controlled volumes of liquid. The drugs used may be very important, such as analgesics, anesthetics including opiates, anti-inflammatory agents, insulin, anti-spasmodic drugs, antibiotics, chemotherapy agents, cardiovascular drugs, and the like. Many of these drugs are needed in very low doses on a continuous basis, so that the patient has a steady, reliable stream over a long period of time, such as 0.1 ml per hour. If pulses are used, the dosage rate may be measure in terms of nanoliters or microliters per pulse or bolus. Regardless of whether a small volume or larger volume pump is being used, the accuracy of the pump is to a successful outcome for the patient.

Some infusion pumps have, along the length of tubing, a pumping chamber having an inlet valve and an outlet valve. The infusion fluid is admitted into a length of tubing in the pumping chamber through an open inlet valve and then isolated by occluding the tube by closing the inlet valve at an inlet of the tubing. Then, the outlet valve is opened and a pumping mechanism compresses or otherwise massages the length of tubing in question to pump or expel the fluid from the pumping chamber and towards the patient. Since the inlet is blocked by the closed valve, the liquid can only exit through the outlet, with an open valve. The outlet valve is then closed and the inlet valve and pumping mechanism opened to permit additional fluid to enter the pumping chamber from a fluid source. The above is something referred to as a singe pumping cycle or stroke.

The pumping mechanism can comprise a single pumping member that compresses the tube against a stationary block or platen. In this case the pumping member or platen may have a length substantially similar to that between the inlet and outlet valves. Alternatively, the pumping mechanism may comprise a plurality of pumping fingers or members that compress the tube in sequence. In this instance, particularly if there are sufficient pumping fingers, such that at least one is compressing the tube at all times, there may be no need for an inlet and/or outlet valves.

The accuracy of an overall infusion is dependent upon the accuracy of each pumping cycle. In other words, it is important to know with accuracy the volume of fluid pumped with each pumping cycle, to know over time the volume of the entire infusion. The volume of each pumping cycle is dependent upon the internal diameter of the tube. A problem arises due to the variability of internal diameters from tube to tube. This variability is due to, among other things, manufacturing processes and tolerances. It would be helpful for the infusion pump to be capable of determining, or measuring the internal diameter of the specific IV tube being utilized for a specific infusion. Based on this information, the pump could adjust the functionality of the pumping mechanism (speed and stroke length of the pumping mechanism) to ensure and maintain accuracy regardless of tubing inner diameter variability.

Additionally, the pump can use this information to avoid overly compressing the tube (decreases tube life due to overstressing) and under compressing the tube (leads to inaccuracies and inefficiencies).

Infusion pumps are used to accurately infuse medicines and other liquids to patients. The amount that is dispensed could be improved by an accurate knowledge of the inner dimensions of the particular tubing used to dispense a particular liquid to a patient.

SUMMARY

The present disclosure includes an infusion pump that can deliver a prescribed amount of medicine, such as insulin or morphine, to a patient. The pump accurately delivers the prescribed amount of the proper medicine in order to insure the best possible outcome for the patient. The pump operates with tubing, and in particular with a contact length of the tubing, to convey the medicine from a source, such as an intravenous ("IV") container, through the contact length, such that medicine does not contact air, risking exposure to contaminants to the patient. The tubing is made typically by extruding the plastic material through a die. The dimensions of the resulting tubing, such as the inner diameter or the outer diameter, can vary by as much as three or four percent. The present pump overcomes this problem by determining the actual dimensions of the contact portion of the tubing during use.

The infusion pump operates with at least one sensor that measures the distance between physical constraints holding the tubing at the contact area. The physical constraints can include a stationary surface or platen and a moving surface or platen between which the tubing is compressed and decompressed. In particular, one method and corresponding system includes the steps of loading tubing into a fixture, compressing the tubing between opposed surfaces of the fixture, receiving a signal indicative of compression of the tubing while compressing, receiving a signal indicative of a contact length of the tubing against at least one of the opposed surfaces, and calculating a diameter and a thickness of the tubing.

Another method and corresponding system includes steps of loading tubing into a fixture, compressing the tubing between opposed surfaces of the fixture, generating and receiving a signal indicative of a distance between the opposed surfaces while compressing, generating and receiving a signal indicative of a contact length of the tubing against at least one of the opposed surfaces, and calculating an inner diameter and a thickness of the tubing.

The methods are systems as discussed are particularly well suited for an infusion pump. The infusion pump includes a tubing clamping section having a moveable portion and a stationary portion, a first sensor mounted on one of the movable portion or the stationary portion for detecting a distance between the movable portion and the stationary portion, at least one second sensor for detecting a contact length of tubing with at least one of the movable portion and the stationary portion, an inlet valve, an outlet valve, and a shuttle having a shuttle stationary portion and a shuttle moveable portion configured for squeezing a length of tubing between the shuttle stationary portion and the shuttle movable portion, wherein the shuttle moveable portion moves toward and away from the shuttle stationary portion to operate the infusion pump.

The infusion pump alternatively includes a housing, a tubing clamping section having a movable portion and a stationary portion, the tubing clamping section mounted on the housing, a first sensor mounted on one of the movable portion or the stationary portion for detecting a distance between the movable portion and the stationary portion, at least one second sensor for detecting a contact length of tubing with at least one of the movable portion and the stationary portion, and a positive displacement pump for manipulating the tubing to accurately deliver a medicament.

It is accordingly an advantage of the present disclosure to provide a system and method for compensating for tubing manufacturing variations in determining medical fluid volume pumped via a tubing pump.

It is another advantage of the present disclosure to provide a system and method for compensating for tubing loading variations in determining medical fluid volume pumped via a tubing pump.

Additional features and advantages are described herein, and will be apparent from the following Detailed Description and the figures.

DETAILED DESCRIPTION

Figure 1:
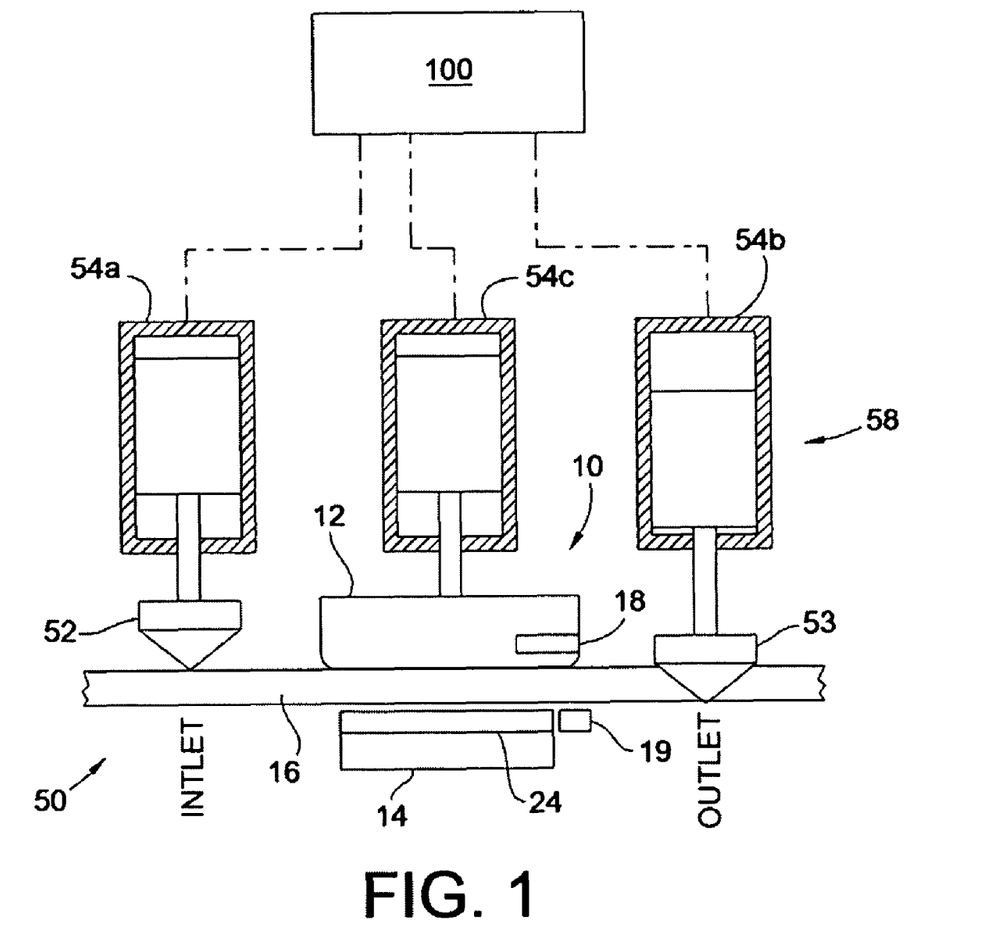
FIG. 1 is an elevation view of a shuttle-type infusion pump having a tubing measurement system and method of the present disclosure.

Referring now to the drawings and in particular to FIG. 1, an embodiment of a shuttle-type infusion pump 50 of the present disclosure is illustrated. Infusion pump 50 includes tubing 16, an inlet valve 52, an outlet valve 53, and a shuttle portion 10 having an upper moving platen 12 and a lower stationary platen 14. Valves 52 and 53 and the shuttle portion 10 are actuated by linear actuators 54a to 54c, respectively. A pump controller 100, which can operate with other processors of infusion pump 50, such as a supervisory processor and a safety processor (not shown), controls pump 50 and its linear actuators 54a to 54c.

To pump fluid, actuator 54a opens inlet valve 52. Actuator 54b closes outlet valve 53 and actuator 54c retracts platen 12, allowing tubing 16 to open to receive a liquid medication, e.g., via gravity. Actuators 54a and 54b then cause the states of valves 52 and 53 to reverse, respectively, and actuator 54c pushes platen 12 towards platen 14 to compress tubing 51, dispelling the volume of fluid that just filled tubing 51 between platens 12 and 14.

As discussed in detail below, a sensor 18, 19 (e.g., sensor pair) is imbedded into moving platen 12 and stationary platen 14. A transmitter 18 can be attached to moving platen 12, while a receiver 19 is in turn attached to stationary platen 14. In use, as the shuttle moving platen 12 closes tubing 51 to pump the liquid to be infused into the patient, the transmitter 18 and receiver 19 respectively send and receive signals and detect the distance between the pair as discussed below. At the same time, a sensor array 24, which is comprised of multiple sensors, detects the length of the tubing segment in contact with platens 12 and 14, also discussed below. In this manner, sensor 18, 19 and sensor array 24 detect and measure the tubing compression distance and contact length, which are sent to controller 100 to calculate an accurate volume of solution actually pumped. This sensing can be repeated for each pump stroke. Pump controller 100 then integrates the accurately determined volumes to adjust the frequency and/or distance of movement of moving platen 12 to ensure accuracy.

Figure 2:
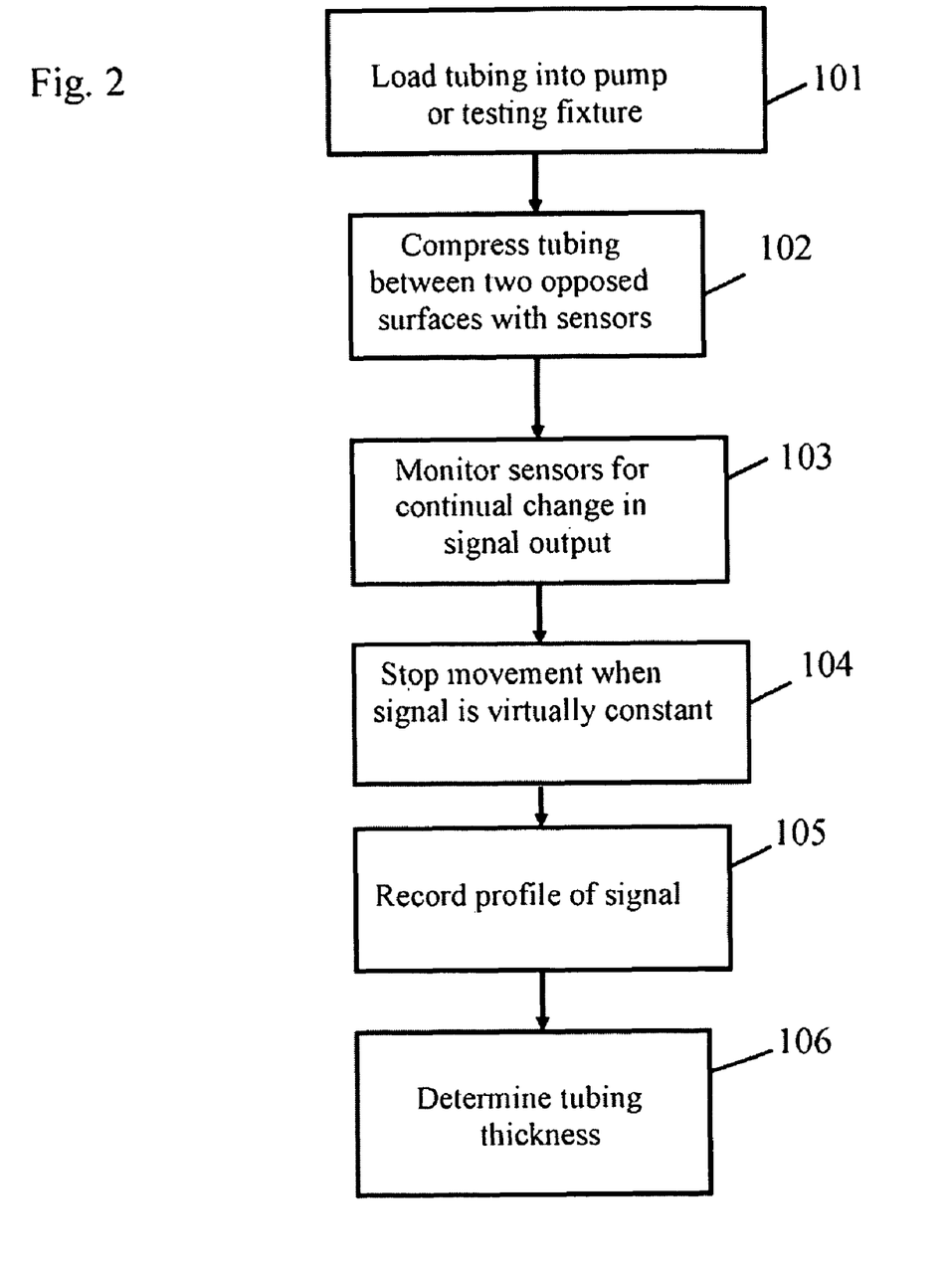
FIG. 2 is a schematic flow diagram illustrating, in a general way, an algorithm used by a pump controller to perform the tubing measurements of the present disclosure.

Referring now to FIG. 2, a high-level flowchart shows one embodiment of an algorithm or process flow diagram that is performed by controller 100 for the multitude of embodiments discussed herein. A first step 101 in the process is to load the tubing into shuttle portion 10 discussed above. Once loaded, the tubing is compressed at step 102 between two opposed surfaces with sensors that measure a distance between the surfaces, and that measure a contact length between the tubing and at least one of the surfaces. While the testing is taking place, controller 100 monitors the sensors at step 103 for changes in signal output. Movement of the surfaces may be stopped, as seen at step 104, when there is almost no change in the signal. The signal is then be recorded at step 105, and controller 100 performs calculations to determine the contact length of the tubing, the thickness of the tubing, and its outer and inner diameters, as seen at step 106. Controller 100 then calculates a volume of liquid actually pumped using the above actual dimensions and adjusts future pumping (e.g., stroke frequency) to make an actual overall volume equal a target overall volume of fluid pumped.

Figure 3A:
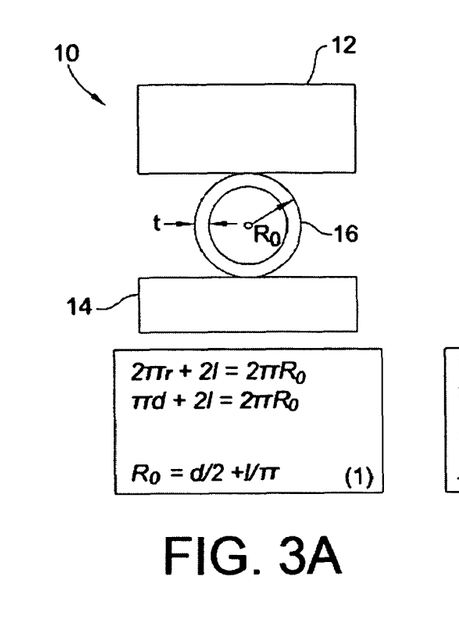
FIGS. 3A, 3B and 4A to 4C are elevation section views of the tube contact portion of the shuttle-type pump infusion pump of FIG. 1, depicting the compression of tubing in a fixture.
Figure 3B:
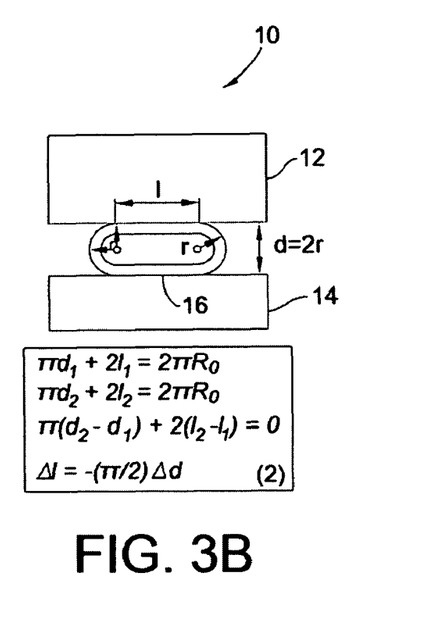

Referring now to FIGS. 3A and 3B, shuttle portion 10 of the infusion pump 50 of FIG. 1 is shown in more detail and includes a lower platen, stationary platen 14 and an upper, moving platen 12, which operate with tubing 16. The lower platen 14 is parallel to the upper moving platen 12 in the illustrated embodiment. Tubing 16 is typically PVC, but may also be made from polyethylene, polypropylene, another medically-acceptable plastic, or a combination of these. In FIG. 3A, prior to compression, tubing 16 has a tubing thickness t and an outer radius $R_0$ when placed initially into shuttle portion 10.

When the movable platen 12 is closed, as shown FIG. 3B, tubing 16 is compressed. In both FIGS. 3A and 3B, d is the distance between the upper and lower platens 12 and 14, r is the radius of the continuously changing tubing curves, and wherein the points at which the tubing separates from the platens defines a tangential contact distance of the tubing with the platens. As shown by the arrows on the left and right side of tubing 16, a length l of the tubing defines such contact distance with the upper and lower platens 12, 14, and wherein the edges of length l define tangential release points.

The equations shown in FIGS. 3A and 3B will now be explained. The continuously changing curves at the sides of tubing 16 extend from contact lengths of the tubing that contact lower and upper platens 14 and 12, which are parallel to teach other. Thus, the newly formed curves are semi-circles with a radius r, which is equal to half the distance d between the platens. The curve length of each newly-formed semi-circle is equal to πr, and the total length of both semicircles or ends is 2πr. The equations shown in connection with FIG. 3A express the following: the total outer curve length of the tubing 16 will not change during compressing, the total outer curve length equal to its circumference when the tubing 16 is in the shape of a circle equals $2\pi R_0$. When the tubing is compressed to a position as shown in the right-hand portion of FIG. 1, the total outer curve length equals the length of the two newly-formed semicircles, 2πr (or πd)+twice the contact length l. Solving for $R_0$, the actual radius of the tubing, it is seen that $R_0$ is d/2+l/π. In FIG. 3A, the tubing 16 is just tangent to the platens 12, 14. In this case, the distance d between the two platens is exactly the outer diameter, $2R_0$, of tubing 16. The contact length is thus zero and twice this length, 2l, is also zero. Therefore, the circumference of the tubing is π times measured distance d, the diameter, equal to 2πr, or in this instance, $2\pi R_0$. The area within a plane of the tubing is π times the inner radius squared, and the volume is calculated by multiplying by the length of tubing or the length of liquid that is propelled by the infusion pump.

To measure the tubing diameter by this method, the tubing in theory can be compressed to any position. As shown in equation block 2 of FIG. 3B, contact lengths $l_1$, $l_2$ are taken at two different distances, $d_1$ and $d_2$. The difference in contact lengths $l_1$ and $l_2$ is proportional to the difference in platen distance d during the step of compressing. Using these corresponding values, the change in contact length l can be determined by the change in platen distance d. In addition, when measuring tubing diameters with this method, multiple tests can be performed by compressing tubing to many different positions, and then using an average of all the calculations to arrive at a more accurate value.

Figure 4A:
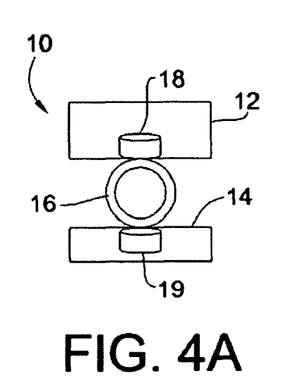
Figure 4B:
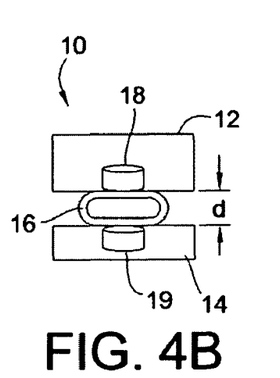
Figure 4C:
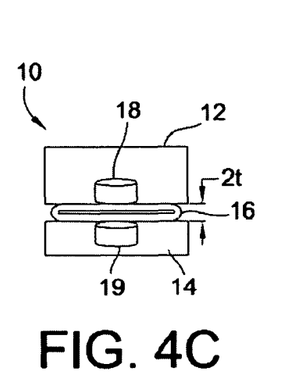

FIGS. 4A to 4C depict a typical situation in which tubing 16 is compressed when moveable pump platen 12 is closed, squeezing tubing 16 against lower fixed platen 14. The distance d between the platens 12, 14 is measured by an ultrasonic sensor (sensor pairs 18 and 19) in this embodiment with a transmitter 18 located with top platen 12 and a receiver 19 located with bottom platen 14. Many infusion pumps already include an ultrasonic sensor, which is used as an air-in-line sensor. This often times pre-existing sensor can be used for sensor 18, 19 of infusion pump 50 (FIG. 1). Other embodiments may use a capacitive sensor, linear transducers such as linear variable differential transformer ("LVDT"), or other distance-measuring sensor. As upper platen 12 is lowered, tubing 16 is flattened, as seen in FIG. 4B, to a distance d.

When moveable platen 12 is completely lowered, as shown in FIG. 4C, tubing 16 compresses such that platens 12, 14 are separated by only the tubing 16 itself, and the distance d is twice the thickness t of the tubing wall. Controller 100 can use sensor 18, 19 to see that the distance d is no longer changing and determine that tube 16 is compressed fully as seen in FIG. 4C. Even before full compression, distance sensor 18, 19 shows that the distance d, is changing very slowly as platens 12 and 14 closely approach each other, separated only by the thickness of the tubing itself, with no air or liquid within. As discussed with FIG. 1, actuator 54c applies a force to upper platen 12, to close the platen against fixed platen 14. A force sensor can also or alternatively be provided and look for an increase in force to signal the complete compression of FIG. 4C. A power or current draw of actuator 54c can also or alternatively be monitored to look for an increase in current draw, indicating full compression.

Figure 5A:
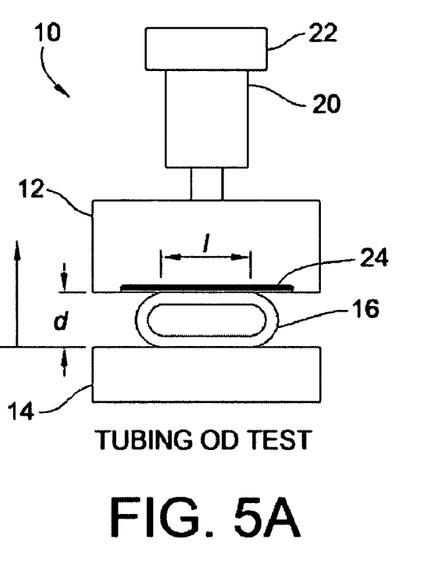
FIGS. 5A and 5B are elevation section views depicting one embodiment of an apparatus and method for measuring tubing compression.
Figure 5B:
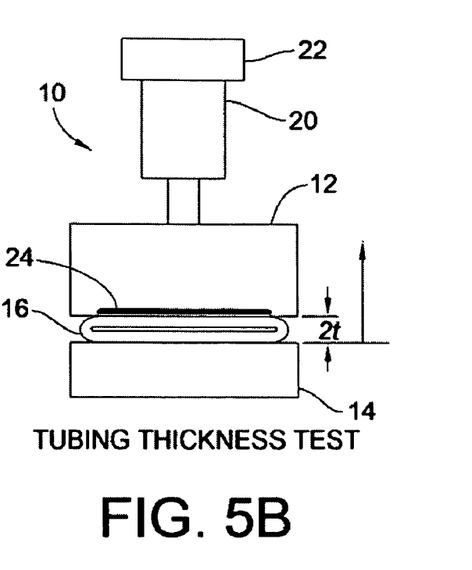

There are still further alternative ways to determine the distance traveled, or amount of tubing compression, as shown in FIGS. 5A and 5B. As before, shuttle portion 10 includes a moving upper portion or platen 12, a bottom platen 14, and tubing 16. Here however, platen 12 is propelled by a motor 20 (e.g., linear) with an encoder 22. The motor may include a lead screw, a ball screw, jackscrew, and so forth, to convert rotational motion to translational motion, to move platen 12 against tubing 16. Motor 20 and encoder 22 are connected to controller 100, shown above, which provides positional information that controller 100 can use and also convert to rate information. Controller 100 controls motor 20 and records data from encoder 22, regarding the shaft of position of motor 20 and converts that position, or change in position into an accurate calculation of the change in translational position of platen 12. Beginning from a known position, the travel and position of the platen 12 can be determined at any time using the information from the encoder, tracking an recoding distance d over many, many discrete time segments during the compression of tubing 16.

Figure 6:
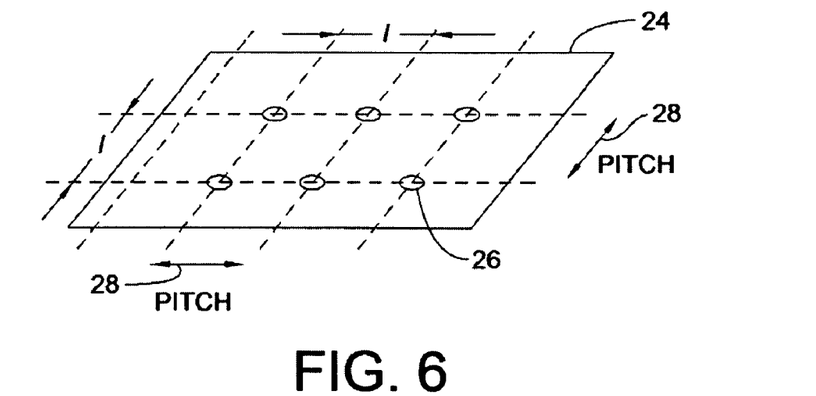
FIG. 6 is a perspective view illustrating a planar sensor array for use in the embodiment of FIGS. 5A and 5B.

FIGS. 5A, 5B and 6 show a sensor array 24. Sensor array 24 includes at least two sensors 26 separated by a distance l. As shown in FIG. 6, there may be one or more columns or rows of at least two sensors 26 each, each column or row separated by a distance l, which may be the same or may be different. For many applications, a single row of two sensors 26 may be adequate. The two sensors 26 detect the presence of tubing 16 between the sensors 26. When the tubing 16 no longer in contact with the sensors 26, the sensors 26 will not indicate the presence of the tubing. This situation may occur the tubing has only tangential contact points with platens 12 and 14. The distance l between the sensors 26 may be set at the length in which the edges of the tubing are just in contact with the sensors when the distance d between the platens is 2t. For a given tubing configuration, with known inner and outer diameters and wall thickness, the platens 12, 14, will be separated by a distance d when there is a known amount of tubing compression, the tubing length reaches length l, and the tubing thickness is about 2t. To set the distance l, measurements may be taken and calibration data points used to measure the length of tubing l in contact with the platens and sensors when the platens are separated by a distance d and the tubing 16 in contact with the platens has thickness 2t.

The sensors 26 of array 24 are capable of detecting the presence of the tubing when the tubing presses against platens 12 and 14 of shuttle portion 10. For example, small compact pressure sensors, capacitive or inducting sensors may be used. Sensors 26 detect the presence of the flattened-out portion of tubing 16 shown above. Sensors 26 will cease to detect the presence of tubing 16 when the tubing is only tangentially contacting the platens. A pressure sensor 26, for example, will show a rapid rise or run-up in pressure when tubing 16 contacts the sensor. When the pressure is removed, the fall-off of pressure and the pressure signal will be just as rapid. A capacitive sensor 26 will operate in a similar manner, with a rapid detection of tubing material, especially wet material, as the tubing approaches the capacitive sensors, e.g., two capacitive sensors 26 spaced apart a known distance l.

Figure 7A:
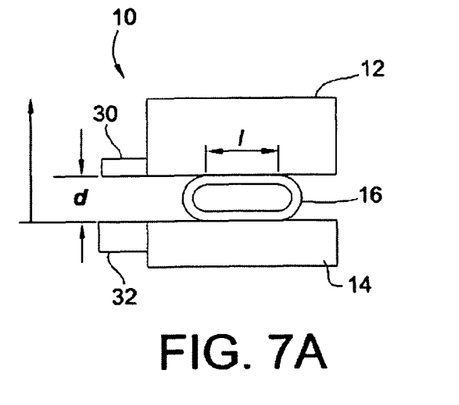
FIGS. 7A and 7B are elevation section views depicting one embodiment of an apparatus and method for measuring a distance between two platens.
Figure 7B:
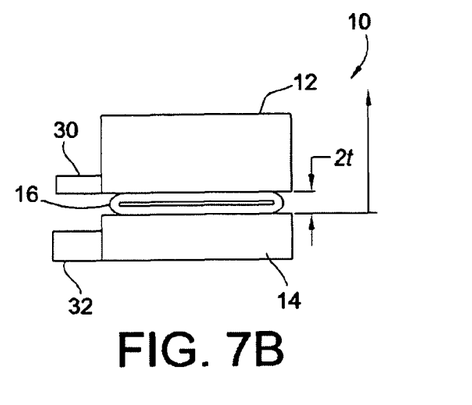

Besides sensor array 24 depicted above, there are other approaches that may be used to detect contact length and tubing compression. FIGS. 7A and 7B depict shuttle portion 10 again having a stationary platen 14, a moving platen 12, and a length of infusion pump tubing 16. In the illustrated embodiment, a capacitive sensor 30 is mounted on the top or moving platen 12, and a target 32 is mounted on the lower, stationary platen 14. When top platen 12 is lowered into place to squeeze tubing 16, capacitive sensor 30 detects the target 32 on bottom platen 14. Calibration of pump 50 (FIG. 1) with sensor 30 makes accurate detection using a capacitive sensor possible. It will be recognized that in this configuration, other proximity sensors may be used, e.g., inductive and ultrasonic sensors. Such proximity sensors are small and unobtrusive relative to the operation of infusion pump 50 (FIG. 1). Target 32 is equally unobtrusive. For example, target 32 may simply be a small bead or square of metal molded into platen 14 or other part of the body of infusion pump 50 located near moving platen 12.

Figure 8A:
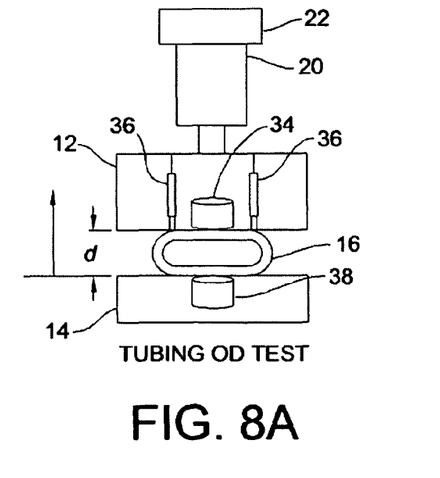
FIGS. 8A and 8B are elevation section views depicting one embodiment of an apparatus and method for measuring a distance between two platens and a contact length of the tubing with the upper platen.
Figure 8B:
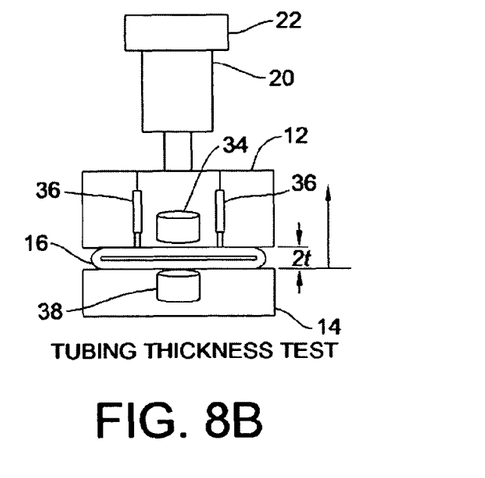

Another apparatus and method for determining the contact length and distance is depicted in FIGS. 8A and 8B. Here again, shuttle portion 10 includes a top platen 12 and bottom platen 14, which receive round plastic tubing 16. Top platen 12 is equipped with two types of sensors, a proximity sensor 34 and two microswitches 36. Bottom platen 14 is equipped with a mating sensing object 38 for proximity sensor 34. If proximity sensor 34 is a capacitive sensor, for example, sensing object 38 is a target suitable for being detected by a capacitive sensor, e.g., a thin metal plate or conductive area. If the bottom platen 14 is metal, inductive or capacitive sensors can sense platen 14 itself without a separate target.

Top platen 12 also includes two microswitches 36. The microswitches are small limit switches that are triggered as the contact portion of tubing 16 approaches (tube closing) or leaves (tube opening) the bottom surface of the top platen 12. Thus, microswitches 36 operate similar to sensor array 24 discussed above, with the distance between the microswitches acting as the distance l of the sensor array. Further alternatively, a linear variable differential transformer ("LVDT"), sometimes also called a linear voltage displacement transformer, may also be used to determine distance d between platens 12 and 14.

Figure 9:
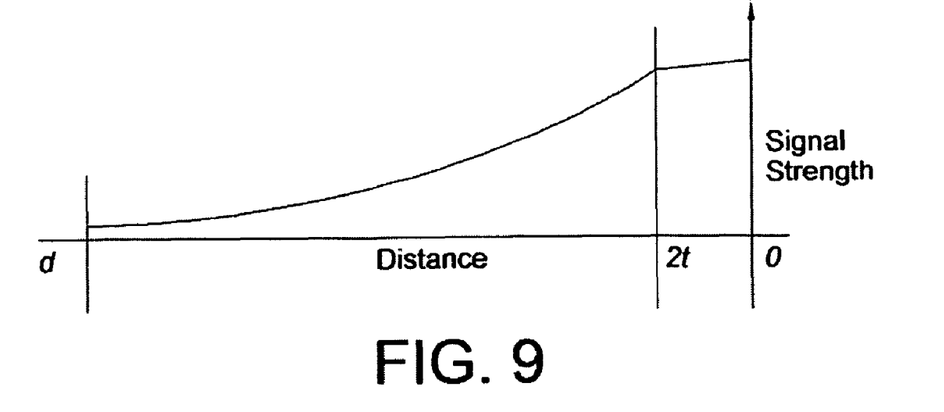
FIGS. 9 to 11 are graphical views depicting sensor readings taken in the above apparatus and methods.

Sample readings of the various sensors described in connection with the above figures are discussed with reference to FIGS. 9 to 11. In FIG. 9, a proximity sensor is used to sense the approach moveable platen 12 towards stationary platen 14. The approach may not be linear, and a somewhat nonlinear signal is shown. However, the signal tends to change very little when the two platens are very close. That is, the distance changes non-linearly down to distance 24 and that remains constant between 2t and a fictitious zero distance. Controller 100 can therefore be configured to look for change or delta d to go to zero to determine that tubing 16 is compressed completely. Thus, in one embodiment, when the proximity sensor signal strength is constant to within a certain amount or percentage, the 2t distance is inferred. This pattern holds true for capacitive sensors, inductive sensors, ultrasound sensors, for example.

Figure 10:
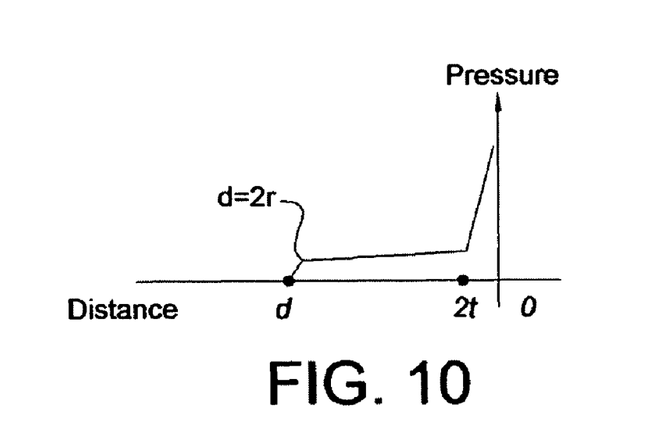

In FIG. 10, a pressure sensor reading is disclosed. In this embodiment, a pressure sensor, for example as part of sensor array 24, reads a zero value, rising to a very low value, as shown, at the point of tangency d=2r (FIG. 3B). When platen 12 continues to close, the pressure rises as the tubing is compressed from d=2r to d=2t until a very rapid rise occurs when the 2t distance (tubing compressed flat) is reached.

Figure 11:
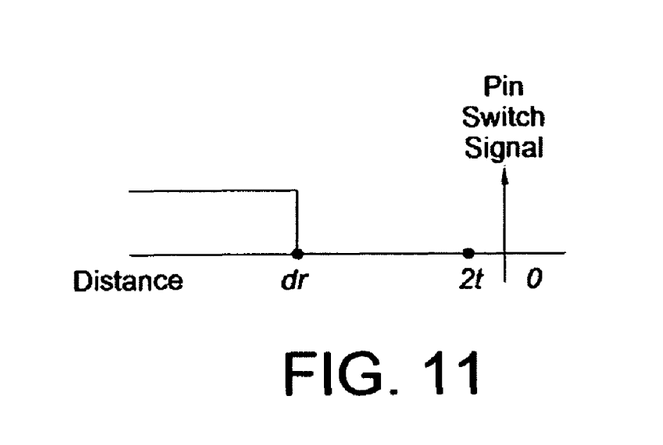

FIG. 11 depicts readings for a microswitch, which will switch on or off as desired when the tubing compresses the contact. In the illustrated instance, the switch is normally on, and as platen 12 closes, the switch remains on, with a constant signal, until the point of tangency is reached (d=2r), at which point the switch is tripped off. The switch then remains off between d=2r and d=2t, even past the point of 2t, until platen 12 opens and the microswitch is reset.

Figure 12A:
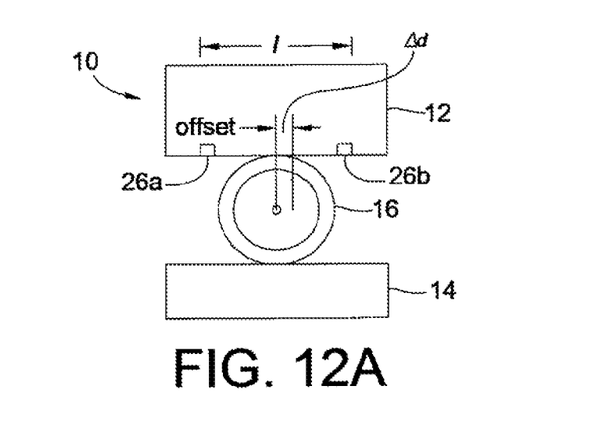
FIGS. 12A to 12D are various views depicting one system and method for correcting tubing offsets.
Figure 12B:
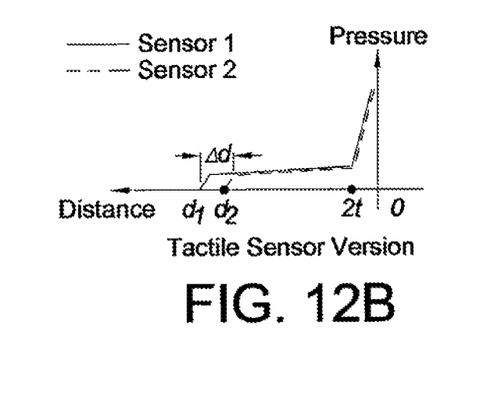
Figure 12C:
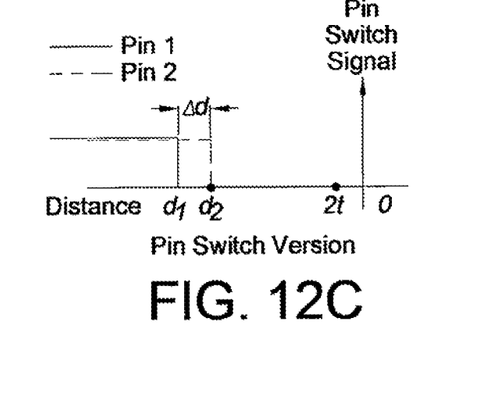
Figure 12D:
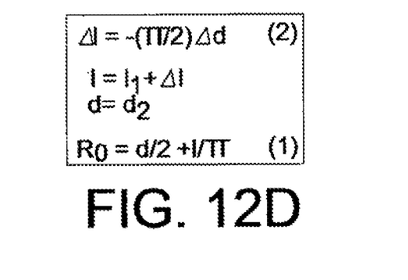

The present disclosure also covers a situation in which tubing 16 does not sit squarely in the center of shuttle portion 10. FIG. 12A, for example, depicts upper and lower platens 12, 14, in which the tubing 16 is offset a distance Δd to the left. Sensors 26a and 26b (e.g., pressure sensors) will notice the offset. FIG. 12B shows that an array 24 of two pressure switches 26a and 26b separated by distance l picks up the pressure at different times. In this instance, tubing 16 is offset to the left and the first sensor, pressure sensor 26a on the left, detects the pressure first, at a different time and distance from the pressure detected by sensor 26b on the right. In FIG. 12C, if two pin-type microswitches are used, as in FIGS. 8A and 8B, switch 36 on the left is tripped by the tubing before switch 36 on the right is tripped. In this case, the real tubing contact length will be equal to l+Δl, where l is the distance between the two sensors (FIG. 12A), and Δl is the extra contact length caused by the time difference between the time when the first sensor on the left detects pressure and the time when the second sensor on the right detects pressure as shown in FIG. 12D. The extra length of tubing in contact with the platen is Δl. The difference Δd in platen distance can be measured by the difference in time from when the first and second pressure sensors detect a sharp rise in pressure. Δl is then calculated using Δd, as shown in FIG. 12D. With the total tubing contact length, l+Δl, and the distance between the platens, the tubing diameter can be calculated. Of course, if there is a time delay caused by the offset, the change in distance Δd will be inverse to the change in contact length Δl.

Figure 13:
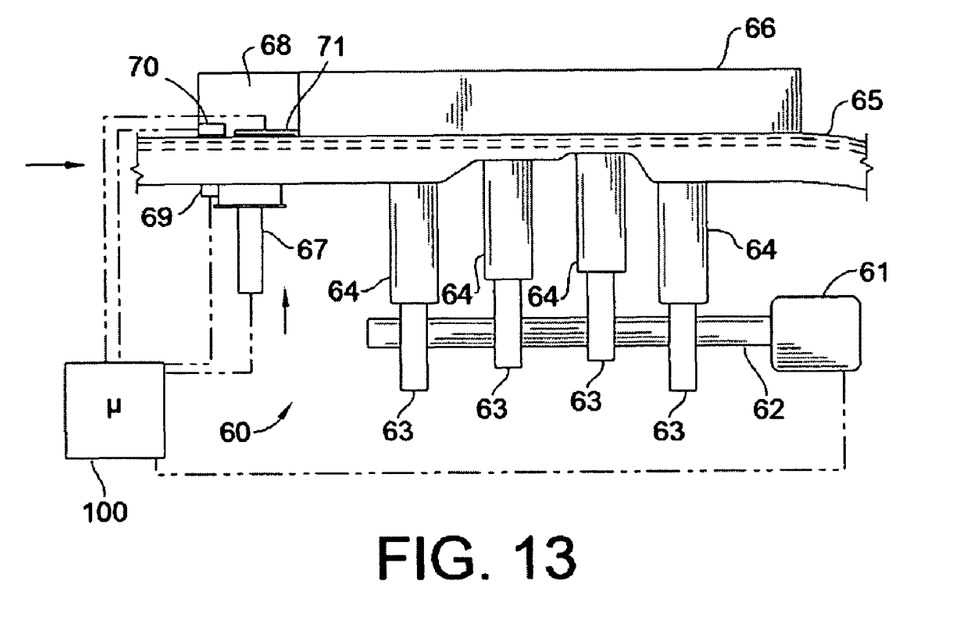
FIG. 13 depicts an alternative cam driven pump embodiment of the tubing measurement apparatus and method of the present disclosure.

Referring now to FIG. 13, the tubing diameter detection of the present disclosure is shown in alternative operation with a linear peristaltic pump 60. Infusion pump 60 includes a motor 61, a drive shaft 62, and a plurality of cam plates 63 for pressing pump rods 64 against tubing 65. The actuators 64 press against stationary portion 66, successively squeezing infusate from rod to rod. Infusion pump 60 also includes an additional cam plate 67. Pump controller 100 in this embodiment controls motor 61, separate cam plate 67, and receives signals from a proximity sensor 69. Under the command of a controller of the infusion pump, cam plate 67 includes a proximity sensor 69. When the cam plate is urged forward, proximity sensor 69 senses a target 70 in stationary portion 68, which may a portion of stationary portion 66, or may be different. Stationary portion 68 includes length sensor 71, for sensing a contact length of tubing 65 against stationary portion 68. Microprocessor controller 100 receives signals from the sensors 69, 71 and controls the motor 61, the cam plate 67, and the other portions of the infusion pump.

Microcontroller 100 also has a memory, or has access to a memory, for a computer program on a computer-readable medium for storing the formulae discussed above and for calculating the contact length and the diameter of the tubing, as also discussed above. From these readings and calculations, controller 100 calculates a volume of a medication or infusate that has been delivered to a patient.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:
1. A method of measuring tubing, the method comprising:
   loading tubing into a fixture;
   compressing the tubing between opposed surfaces of the fixture;
   receiving a signal indicative of compression of the tubing while compressing;

receiving a signal indicative of a contact length of the tubing against at least one of the opposed surfaces; and calculating a diameter and a thickness of the tubing.

2. The method of claim 1, further comprising monitoring the signal indicative of compression of the tubing or the signal indicative of the contact length.

3. The method of claim 1, wherein the signal indicative of compression of the tubing is indicative of a distance between the opposed surfaces of the fixture.

4. The method of claim 1, wherein the signal indicative of compression of the tubing is generated by an LVDT, an ultrasonic sensor, an air-in-line sensor, or a capacitive sensor.

5. The method of claim 1, wherein the signal indicative of a contact length is generated by a sensor, a pressure sensor, a sensor array, a switch array, or a capacitive sensor.

6. The method of claim 1, wherein the opposed surfaces are part of an infusion pump.

7. The method of claim 1, wherein the step of calculating calculates a diameter of the tubing using two half-circles and a contact length of tubing with the opposed surfaces.

8. A method for measuring a diameter and a thickness of tubing, the method comprising:
  loading tubing into a fixture;
  compressing the tubing between opposed surfaces of the fixture;
  generating and receiving a signal indicative of a distance between the opposed surfaces while compressing;
  generating and receiving a signal indicative of a contact length of the tubing against at least one of the opposed surfaces; and
  calculating an inner diameter and a thickness of the tubing.

9. The method of claim 8, wherein the signal indicative of the distance is generated by an air-in-line sensor.

10. The method of claim 8, wherein the signal indicative of the contact length is generated by at least one sensor array.

11. The method of claim 8, further comprising calculating a volume of liquid infusate using the calculated inner diameter.

12. An infusion pump, comprising:
  a tubing clamping section comprising a movable portion and a stationary portion;
  a first sensor mounted on one of the movable portion or the stationary portion for detecting a distance between the movable portion and the stationary portion;
  at least one second sensor for detecting a contact length of tubing with at least one of the movable portion and the stationary portion;
  an inlet valve;
  an outlet valve; and
  a shuttle comprising a shuttle stationary portion and a shuttle moveable portion configured for squeezing a length of tubing between the shuttle stationary portion and the shuttle movable portion, wherein the shuttle moveable portion moves toward and away from the shuttle stationary portion to operate the infusion pump.

13. The infusion pump according to claim 12, wherein the first sensor comprises an LVDT, an ultrasonic sensor, an air-in-line sensor, or a capacitive sensor.

14. The infusion pump according to claim 12, wherein the second sensor comprises a sensor, a pressure sensor, a sensor array, a switch array, or a capacitive sensor.

15. The infusion pump according to claim 12, further comprising a target mounted on the other of the moving portion and the stationary portion.

16. An infusion pump, comprising:
  a housing;
  a tubing clamping section comprising a movable portion and a stationary portion, the tubing clamping section mounted on the housing;
  a first sensor mounted on one of the movable portion or the stationary portion for detecting a distance between the movable portion and the stationary portion;
  at least one second sensor for detecting a contact length of tubing with at least one of the movable portion and the stationary portion; and
  a positive displacement pump for manipulating the tubing to accurately deliver a medicament.

17. The infusion pump according to claim 16, wherein the positive displacement pump is a shuttle pump or a peristaltic pump.

18. The infusion pump according to claim 16, wherein the first sensor is an air-in-line sensor or a proximity sensor.

19. The infusion pump according to claim 16, wherein the at least one second sensor comprises two spaced-apart sensors or microswitches.

20. The infusion pump according to claim 16, further comprising a computer program on a computer-readable disc for calculating a length and a diameter of the tubing.

* * * * *